United States Patent
Wu et al.

(10) Patent No.: US 11,642,497 B2
(45) Date of Patent: May 9, 2023

(54) MULTIPLE WIRE BALLOON DILATION CATHETER

(71) Applicant: DONGGUAN TT MEDICAL INC., Dongguan (CN)

(72) Inventors: Tim Wu, Dongguan (CN); Yuying Bi, Dongguan (CN); Linjuan Hu, Dongguan (CN); Yuanyi Luo, Dongguan (CN)

(73) Assignee: DONGGUAN TT MEDICAL INC., Dongguan (CN)

( * ) Notice: Subject to any disclaimer, the term of this patent is extended or adjusted under 35 U.S.C. 154(b) by 0 days.

(21) Appl. No.: 17/888,208

(22) Filed: Aug. 15, 2022

(65) Prior Publication Data
US 2023/0033740 A1   Feb. 2, 2023

(30) Foreign Application Priority Data
Nov. 9, 2021   (CN) .......................... 202111316724.3

(51) Int. Cl.
*A61M 29/00* (2006.01)
*A61M 25/01* (2006.01)
*A61M 25/10* (2013.01)

(52) U.S. Cl.
CPC ........ *A61M 25/0169* (2013.01); *A61M 25/10* (2013.01)

(58) Field of Classification Search
CPC .......... A61M 25/0169; A61M 25/0172; A61M 2025/0177; A61M 25/10; A61M 25/1011; A61M 2025/1056
See application file for complete search history.

(56) References Cited

U.S. PATENT DOCUMENTS

| | | | |
|---|---|---|---|
| 5,267,958 A | 12/1993 | Buchbinder et al. |
| 5,357,978 A | 10/1994 | Turk |
| 6,071,285 A | 6/2000 | Lashinski |
| 6,221,090 B1 | 4/2001 | Wilson |
| 6,682,556 B1 | 1/2004 | Ischinger |
| 2001/0027291 A1 | 10/2001 | Shanley |
| 2002/0029014 A1 | 3/2002 | Jayaraman |
| 2004/0116915 A1 | 6/2004 | Lentz |

(Continued)

FOREIGN PATENT DOCUMENTS

| | | |
|---|---|---|
| CN | 102188272 A | 9/2011 |
| CN | 204766984 U | 11/2015 |

(Continued)

*Primary Examiner* — Deanna K Hall

(57) ABSTRACT

Disclosed are a multi-guidewire balloon dilatation catheter structure, a dilatation catheter mechanism and a medical device. The multi-guidewire balloon dilatation catheter comprises a balloon, a first guidewire channel, a second guidewire channel and a third guidewire channel. The first guidewire channel is at least partially passed through the balloon. The second guidewire channel is at least partially located at the distal end of the balloon. The third guidewire channel is at least partially located at the proximal end of the balloon. In the multi-guidewire balloon dilatation catheter structure of this embodiment, each guidewire channel can be used for accommodating the guidewire by providing the first guidewire channel and the second/third guidewire channel to assemble various devices on the single catheter of the present invention, thereby realizing simultaneous execution of device guidance, plaque cutting, guidewire anchoring, etc. The structure is simple and good in use effect.

9 Claims, 8 Drawing Sheets

(56) References Cited

U.S. PATENT DOCUMENTS

| | | |
|---|---|---|
| 2004/0143286 A1 | 7/2004 | Johnson |
| 2004/0220473 A1 | 11/2004 | Lualdi |
| 2005/0015108 A1 | 1/2005 | Williams et al. |
| 2005/0154440 A1 | 7/2005 | Limon |
| 2005/0187602 A1 | 8/2005 | Eidenschink |

FOREIGN PATENT DOCUMENTS

| | | |
|---|---|---|
| CN | 208911235 U | 5/2019 |
| CN | 210844886 U | 6/2020 |
| CN | 111672016 A | 9/2020 |
| CN | 113116470 A | 7/2021 |

MULTIPLE WIRE BALLOON DILATION CATHETER

CROSS-REFERENCE TO RELATED APPLICATIONS

This application claims the benefit of priority from Chinese Patent Application No. 202111316724.3, filed on Nov. 9, 2021. The content of the aforementioned application, including any intervening amendments thereto, is incorporated herein by reference in its entirety.

TECHNICAL FIELD

The present invention relates to the technical field of medical devices, in particular to a multi-guidewire balloon dilatation catheter structure, a dilatation catheter mechanism, and a medical device.

BACKGROUND OF THE INVENTION

Percutaneous transluminal coronary angioplasty (PTCA) is the main method for treating the coronary heart disease, which is used to dilate narrowed blood vessel found in patients with coronary artery disease using a coronary dilatation catheter. During a surgical procedure, the coronary dilatation catheter is dilated by using a balloon. It can not only be used to dilate the narrowed blood vessel, but also be used for pre-dilatation prior to stent implantation or post-dilatation after stent implantation.

The coronary dilatation catheter mainly consists of a proximal component, a transition section and a distal component. The distal component and the proximal component are connected by the transition section provided in the middle. The proximal component comprises a hypotube and a handle, and the distal component comprises an inner tube, an outer tube and a balloon. The distal component is guided by the guidewire so that it can reach the focal blood vessel for dilatation.

The traditional dilatation catheters have single functions, such as only guiding the balloon or only cutting. During a surgical procedure, it is usually necessary to use a plurality of dilatation catheters to work with each other. Their disadvantages include: the surgical effect and safety are affected by increased devices in the blood vessel, the harm to the patients caused by multiple insertion of guidewires/catheters into the blood vessel is increased due to the single function of catheters, and the use effect is not good.

SUMMARY OF THE INVENTION

The present invention provides a multi-guidewire balloon dilatation catheter structure, a dilatation catheter mechanism and a medical device, which are used to solve the problems of single function and poor use effect of the traditional dilatation catheters.

The present invention provides a multi-guidewire balloon dilatation catheter structure, comprising:
a balloon;
a first guidewire channel, which is used for accommodating a guidewire and which is at least partially passed through the balloon;
a second guidewire channel, which is used for accommodating a guidewire and which is at least partially located at the distal end of the balloon; and
a third guidewire channel, which is used for accommodating a guidewire and which is at least partially located at the proximal end of the balloon.

According to an embodiment of the present invention, the multi-guidewire balloon dilatation catheter structure further comprises a catheter which is passed through the balloon, and a guidewire exchange port which is formed in the outer wall of the catheter and provided at the proximal end of multi-guidewire balloon dilatation catheter structure, wherein the first guidewire channel is at least partially located in the catheter, and the proximal end of the first guidewire channel is communicated with the guidewire exchange port.

According to an embodiment of the present invention, the distance between the guidewire exchange port and the balloon along the central axis of the multi-guidewire balloon dilatation catheter structure is less than 30 mm.

According to an embodiment of the present invention, the distance between the guidewire exchange port and the balloon along the central axis of the multi-guidewire balloon dilatation catheter structure is 10-20 mm.

According to an embodiment of the present invention, an accommodating cavity communicated with an external air source is provided inside the balloon, and the multi-guidewire balloon dilatation catheter further comprises at least one positioning portion, which is connected to the catheter and which is at least partially located in the accommodating cavity.

According to an embodiment of the present invention, the multi-guidewire balloon dilatation catheter structure further comprises a guidewire member, which is provided outside the balloon and which is at least partially located at the distal end of the balloon, and the second guidewire channel is at least partially located inside the guidewire member.

According to an embodiment of the present invention, there are at least two guidewire members, and two of the guidewire members are respectively provided at opposite ends of the balloon.

According to an embodiment of the present invention, the second guidewire channel or the third guidewire channel is at least partially parallel to the first guidewire channel.

The present invention further provides a dilatation catheter mechanism, comprising:
at least one guidewire; and
the multi-guidewire balloon dilatation catheter structure in any one of the embodiments described above; when there is only one guidewire, the guidewire is inserted into at least one of the first guidewire channel, the second guidewire channel and the third guidewire channel; when there are a plurality of guidewires, the first guidewire channel, the second guidewire channel and the third guidewire channel are inserted into at least one guidewire respectively.

The present invention further provides a medical device, comprising the multi-guidewire balloon dilatation catheter in any embodiments above, or the dilatation catheter mechanism in any embodiments above.

Implementing the embodiments of the present invention has the following beneficial effects:

When the multi-guidewire balloon dilatation catheter structure of this embodiment is used, at least one guidewire can be connected through the multi-guidewire balloon dilatation catheter structure. The multi-guidewire balloon dilatation catheter structure can be guided by means of the cooperation of the guidewire and the first guidewire channel to achieve a corresponding surgical function. When the guidewire is inserted into the second guidewire channel, the guidewire is at least partially located outside the balloon and can guide the multi-guidewire balloon dilatation catheter structure to advance. After the balloon is dilated, the guidewire can be driven to cut the diseased tissue on the inner wall of the blood vessel, or the guidewire can be anchored by the squeezing of the outer wall of the balloon on the inner wall of the blood vessel, so as to facilitate the fitting of the subsequent devices and the guidewire. When the multi-guidewire balloon dilatation catheter structure works with two guidewires, the two guidewires can be passed through the first guidewire channel and the second guidewire channel respectively to meet the surgical needs.

In the multi-guidewire balloon dilatation catheter structure of this embodiment, each guidewire channel can be inserted into the guidewire by providing the first guidewire channel, the second guidewire channel and the third guidewire channel, thereby realizing simultaneous execution of guiding, cutting and anchoring functions of the multi-guidewire balloon dilatation catheter structure. The structure is simple in structure and good in use effect.

In the dilatation catheter mechanism of this embodiment, the multi-guidewire balloon dilatation catheter structure is provided in such a way that the structure can be inserted into at least one guidewire, thereby realizing the guiding, cutting and anchoring functions of the multi-guidewire balloon dilatation catheter structure, and is good in use effect.

BRIEF DESCRIPTION OF THE DRAWINGS

To explain the present invention or the technical scheme in the prior art more clearly, a brief introduction will be made to the embodiments or the drawings that need to be used in the description of prior art. Obviously, the drawings described below are some embodiments of the present invention. For those of ordinary skill in the art, other drawings can also be obtained from these drawings without any creative effort.

IN THE DRAWINGS

Figure 1:
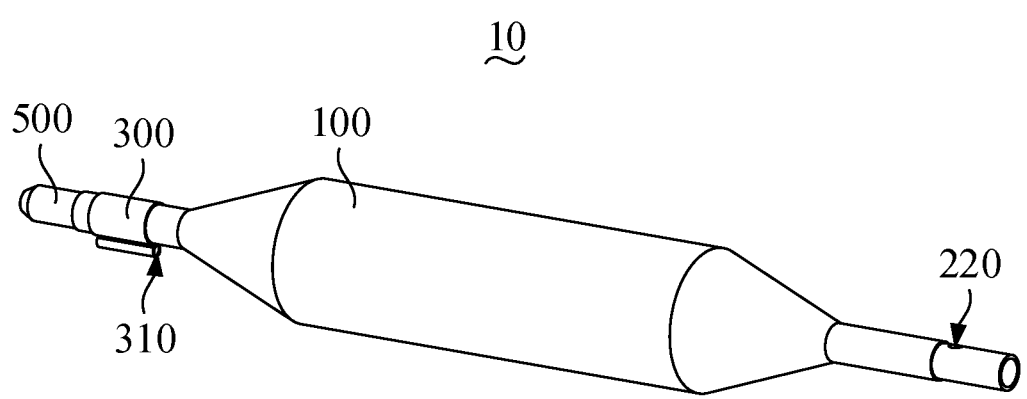
Figure 2:
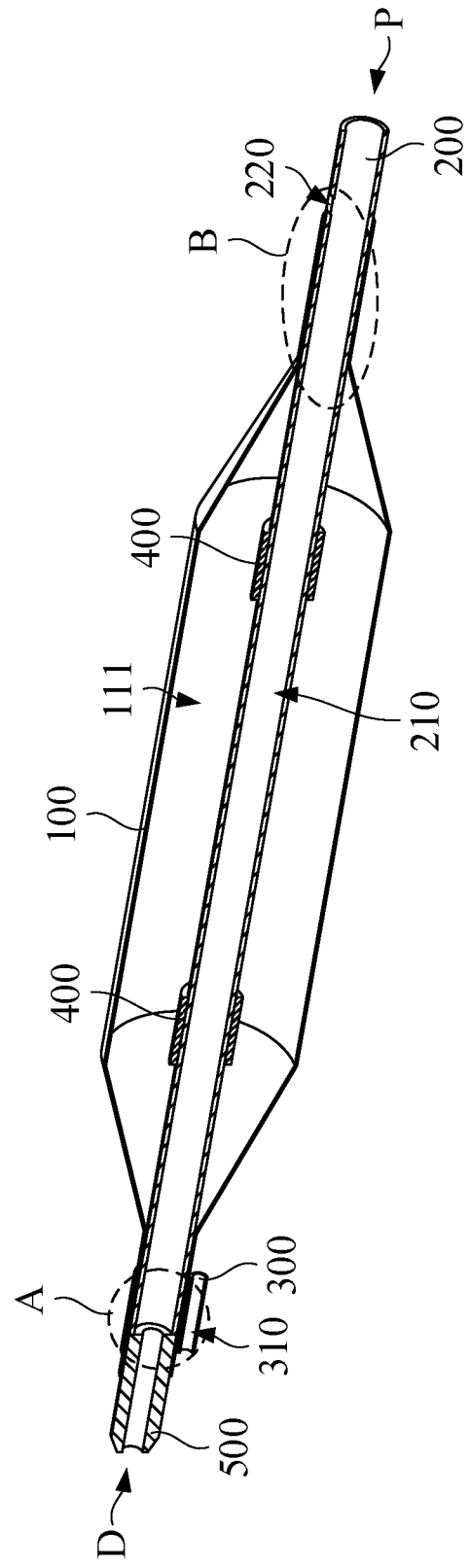
Figure 3:
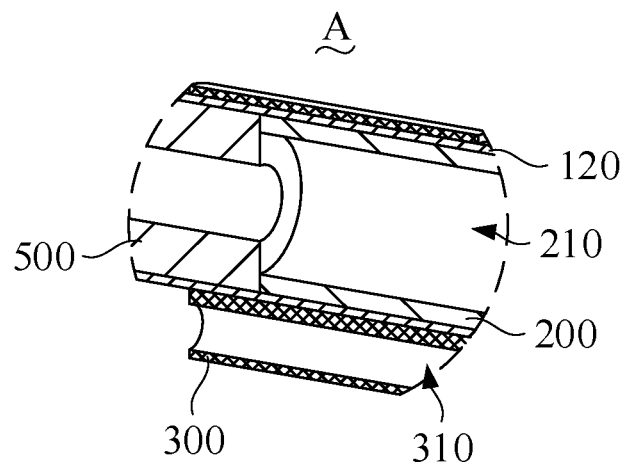
Figure 4:
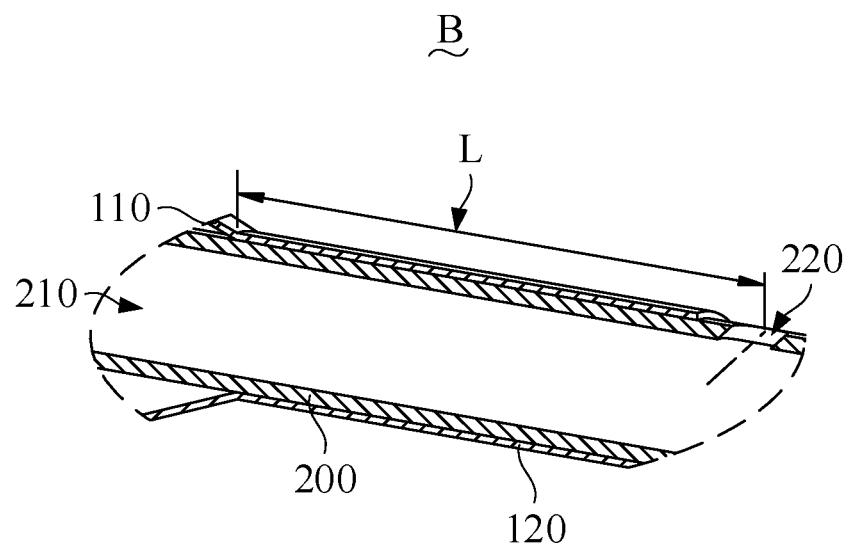
Figure 5:
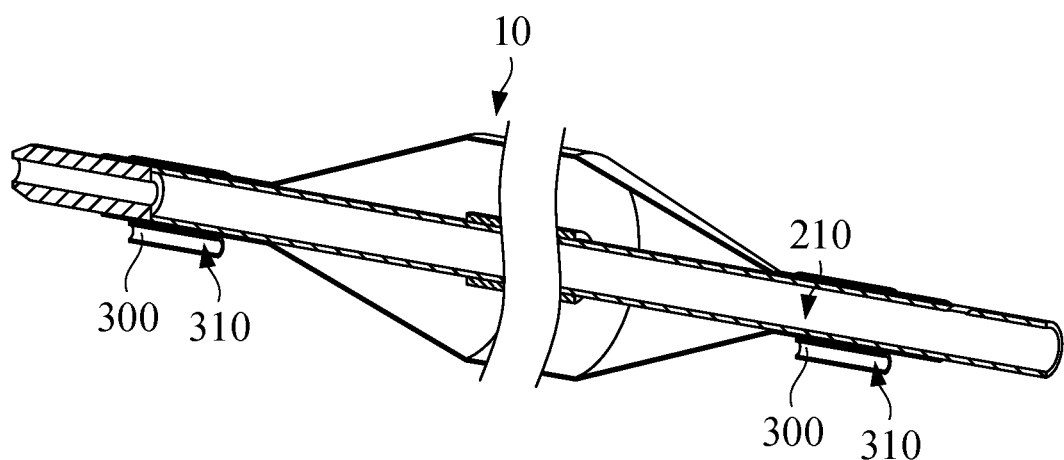
Figure 6:
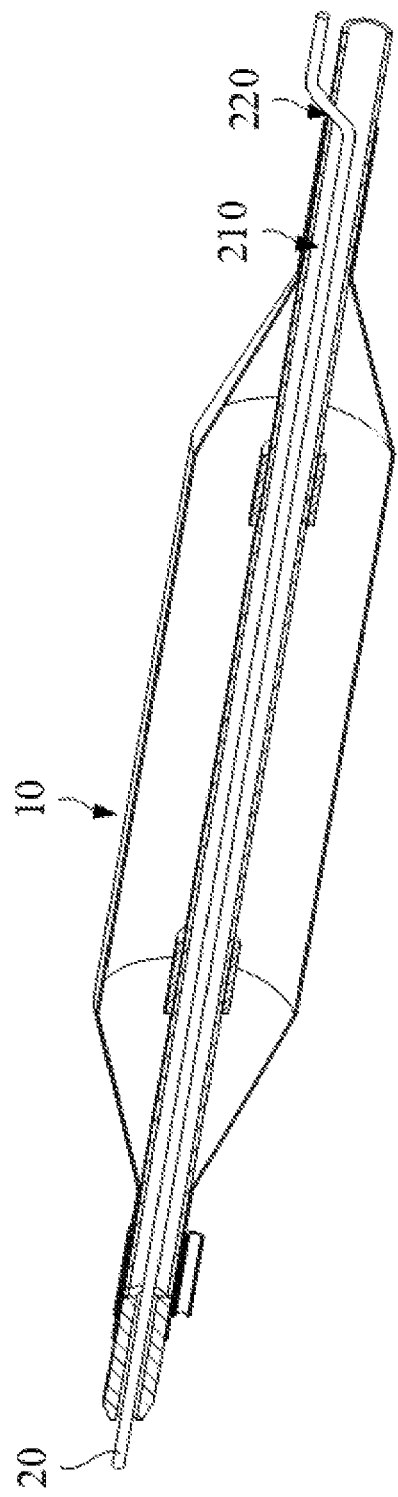
Figure 7:
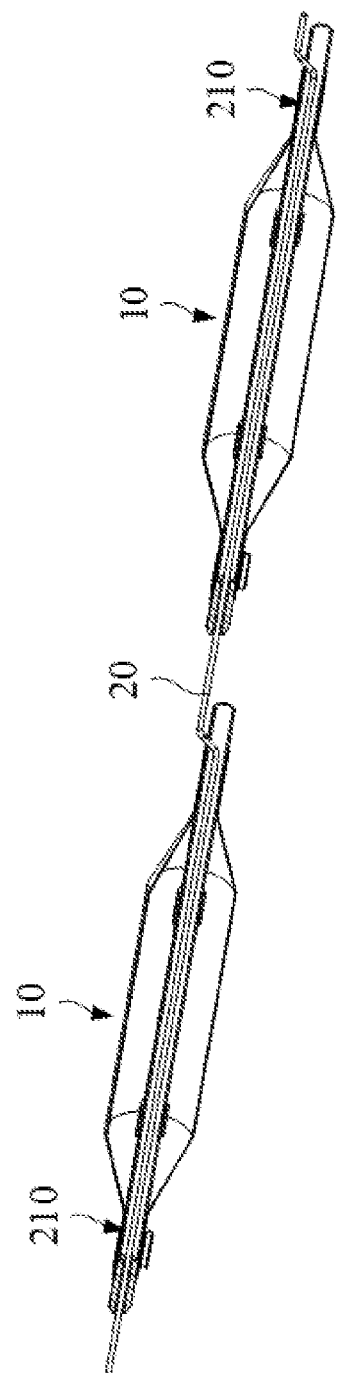
Figure 8:
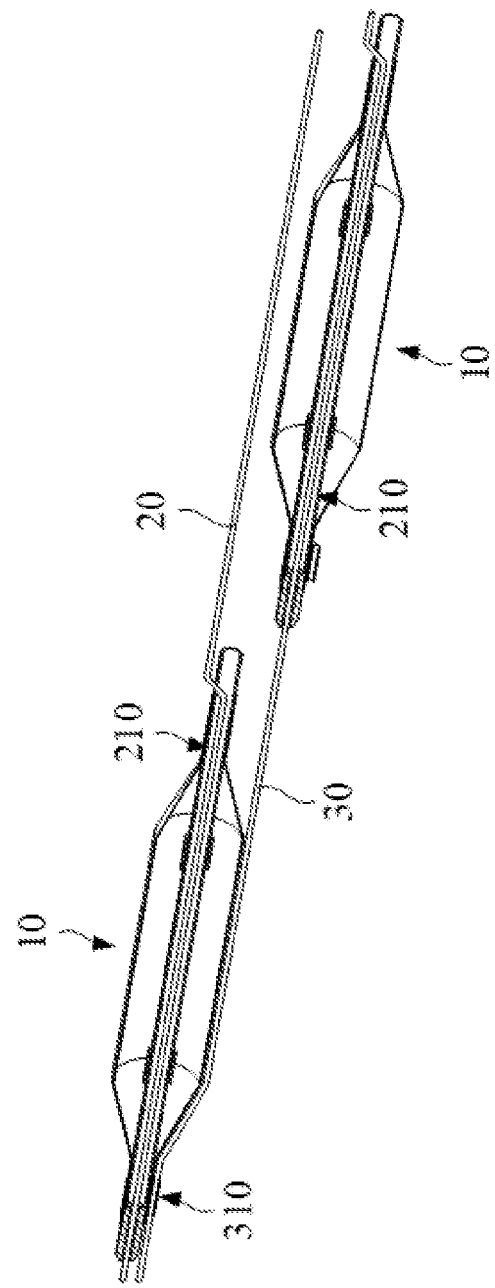
Figure 9:
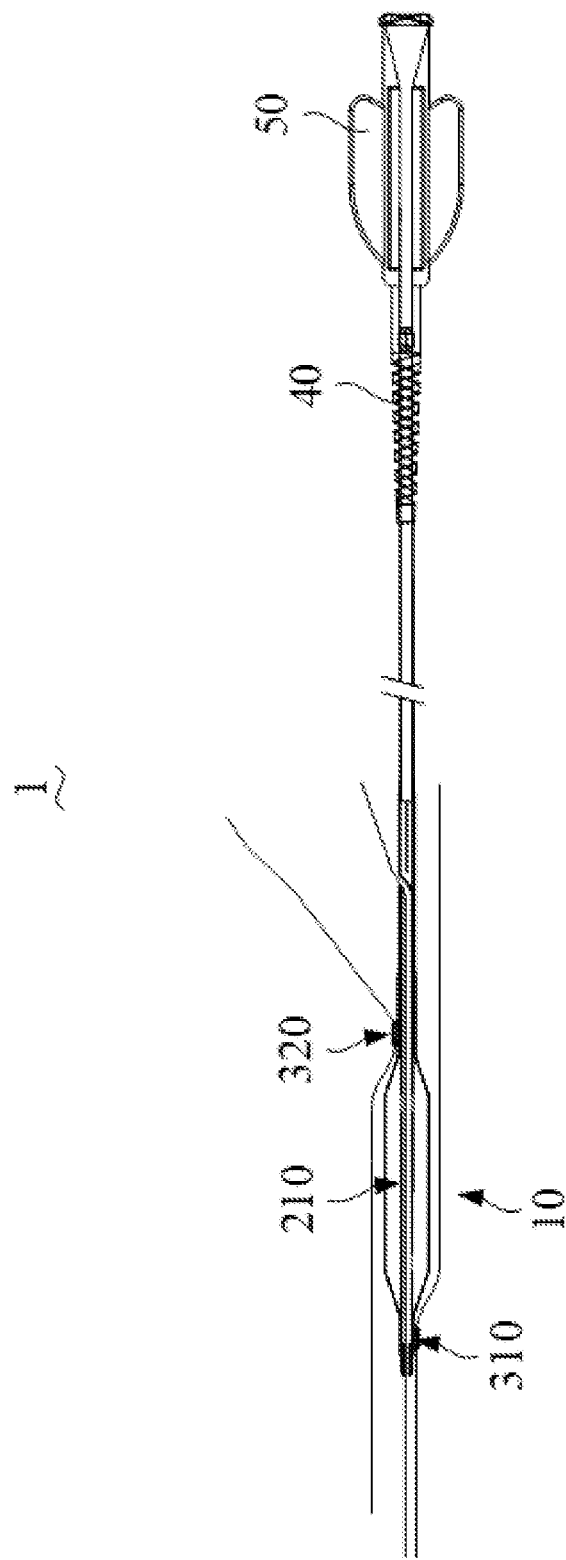

FIG. 1 is an axial view of a multi-guidewire balloon dilatation catheter structure in an embodiment of the present invention;

FIG. 2 is a cross-sectional view of a multi-guidewire balloon dilatation catheter structure in an embodiment of the present invention;

FIG. 3 is an enlarged view of section A in FIG. 2;

FIG. 4 is an enlarged view of section B in FIG. 2;

FIG. 5 is a schematic cross-sectional view of a multi-guidewire balloon dilatation catheter structure in another embodiment of the present invention;

FIG. 6 is a partial structural schematic diagram of the balloon catheter mechanism in use in the first embodiment of the present invention;

FIG. 7 is a partial structural schematic diagram of the balloon catheter mechanism in use in the second embodiment of the present invention;

FIG. 8 is a partial structural schematic diagram of the balloon catheter mechanism in use in the third embodiment of the present invention; and FIG. 9 is a schematic structural diagram of a balloon catheter mechanism in an embodiment of the present invention.

REFERENCE NUMERALS

1. Balloon catheter mechanism;
10. Multi-guidewire balloon dilatation catheter structure;
100. Balloon; 110. Balloon portion; 111. Accommodating cavity; 120. Connecting portion;
200. Catheter; 210. First guidewire channel; 220. Guidewire exchange port;
300. Guidewire member; 310. Second guidewire channel; 320. Third guidewire channel;
400. Positioning portion;
500. Tip tube;
20. First guidewire;
30. Second guidewire;
40. Hypotube;
50. Catheter hub.

DETAILED DESCRIPTION OF THE INVENTION

To make the object, technical scheme and advantages of the present invention clearer, the technical scheme in the invention will be clearly and completely described below with reference to the drawings. It is clear that the described embodiments are part of the embodiments of the invention and not all the embodiments. Based on the embodiments of the present invention, all other embodiments obtained by those of ordinary skill in the art without creative efforts shall fall within the protection scope of the invention.

Referring to FIGS. 1, 2 and 9, the embodiments of the present invention provide a multi-guidewire balloon dilatation catheter structure 10, which comprises a balloon 100, a first guidewire channel 210, and a second guidewire channel 310 and the third guidewire channel 320. Inside the balloon 100 is provided an accommodating cavity 111 that communicates with an external air source. The balloon portion 110 can be dilated by filling the accommodating cavity 111 with gas. The first guidewire channel 210 is at least partially passed through the balloon 100. The second guidewire channel 310 is used for accommodating the guidewire and is at least partially located at the distal end of the balloon 100. The third guidewire channel 320 is used for accommodating the guidewire and is at least partially located at the proximal end of the balloon 100.

It should be noted that, referring to FIG. 2, the D (Distal) end in the figure is defined as the distal end of the multi-guidewire balloon dilatation catheter structure 10, and the P (Proximal) end in the figure is defined as the proximal end of the multi-guidewire balloon dilatation catheter structure 10. The proximal end refers to the end near the surgeon during the procedure, that is, the end near the operating part. The distal end refers to the end away from the surgeon during the procedure, that is, the end near the end of the guidewire.

When the multi-guidewire balloon dilatation catheter structure 10 of this embodiment is used, at least one guidewire can be connected through the multi-guidewire balloon dilatation catheter structure 10. The multi-guidewire balloon dilatation catheter structure 10 can be guided by means of the cooperation of the guidewire and the first guidewire channel 210 to achieve the corresponding surgical function. When the guidewire is inserted into the second guidewire channel 310, the guidewire is at least partially located outside the balloon 100 and can guide the multi-guidewire balloon dilatation catheter structure 10 to advance. After the balloon is dilated, the guidewire can be driven to cut the diseased tissue on the inner wall of the blood vessel, or the guidewire can be anchored by the squeezing of the outer wall of the balloon 100 on the inner wall of the vessel, so as to facilitate the fitting of the subsequent devices and the guidewire. When the multi-guidewire balloon dilatation catheter structure 10 works with two guidewires, the two guidewires can be inserted into the first guidewire channel 210 and the second guidewire channel 310 respectively to meet the surgical needs.

In the multi-guidewire balloon dilatation catheter structure 10 of this embodiment, each guidewire channel can be inserted into the guidewire by providing the first guidewire channel 210 and the second guidewire channel 310, thereby realizing simultaneous execution of guiding, cutting and anchoring functions of the multi-guidewire balloon dilatation catheter structure 10. The structure is simple and good in use effect Particularly, referring to FIG. 2, the multi-guidewire balloon dilatation catheter structure 10 further comprises a catheter 200 which is passed through the balloon 100, and a guidewire exchange port 220 which is formed in the outer wall of the catheter 200 and provided at the proximal end of the multi-guidewire balloon dilatation catheter structure 10, wherein the first guidewire channel 210 is at least partially located in the catheter 200, and one end of the first guidewire channel 210 is communicated with the guidewire exchange port 220.

When the multi-guidewire balloon dilatation catheter structure 10 of this embodiment is used, the guidewire is placed into the blood vessel, and then the P end of the guidewire is inserted into the first guidewire channel 210 from the end of the balloon 100 away from the guidewire exchange port 220, and extends out from the guidewire exchange port 220. Thus, the operating mechanism can be used to advance the multi-guidewire balloon dilatation catheter structure 10 along the guidewire to the lesion for corresponding surgical procedure.

Further, referring to FIGS. 2 and 4, the distance between the guidewire exchange port 220 and the balloon 100 along the central axis of the multi-guidewire balloon dilatation catheter structure 10 is not greater than the length of the balloon 100.

It should be noted that, in a traditional balloon catheter mechanism, the distance between the guidewire exchange port and the balloon is usually 200 mm-300 mm because the structure between the guidewire exchange port and the balloon is usually unfunctional, and the distance is usually greater than the length of the balloon 100, which results in that the space of this section of the balloon catheter mechanism cannot be effectively utilized during use. In this embodiment, the distance between the guidewire exchange port 220 and the balloon 100 is provided to be not greater than the length of the balloon 100, which can reduce the space occupied by this part of structure, and thus reduce the axial length of the multi-guidewire balloon dilatation catheter structure 10 in the blood vessel. For the multi-guidewire balloon dilatation catheter structure 10 of this embodiment, on the one hand, this design can drive the multi-guidewire balloon dilatation catheter structure 10 to exit from the D end of the guidewire, that is, the multi-guidewire balloon dilatation catheter structure 10 advances in the direction from the P end to the D end and is separated from the guidewire, while the traditional balloon catheter mechanism can only exit from the P end, so that the multi-guidewire balloon dilatation catheter structure 10 can meet different clinical surgical needs; on the other hand, since the overall size of the multi-guidewire balloon dilatation catheter structure 10 is reduced, a plurality of multi-guidewire balloon dilatation catheter structures 10 can be used on a single guidewire at the same time, or the multi-guidewire balloon dilatation catheter structure 10 can be used in conjunction with other devices such as stents when treating long lesions, thereby improving surgical efficiency and safety and achieving good use effect.

Particularly, referring to FIG. 4, the distance between the guidewire exchange port 220 and the balloon 100 is less than 30 mm.

In this embodiment, the distance between the guidewire exchange port 220 and the balloon 100 may be 10 mm, 15 mm or 20 mm, which is not defined herein. In this embodiment, the balloon 100 comprises a balloon portion 110 and connecting portions 120. The connecting portions 120 are provided at opposite ends of the balloon portion 110, and the accommodating cavity 111 is located inside the balloon portion 110. The connecting portions 120 are used for connecting the catheter 200. Particularly, the distance L between the guidewire exchange port 220 and the proximal end of the balloon portion 110 is ≤30 mm.

Further, referring to FIG. 2, the multi-guidewire balloon dilatation catheter structure 10 further comprises at least one positioning portion 400, which is connected to the catheter 200 and which is at least partially located in the accommodating cavity 111.

In this way, during a surgical procedure, the surgeon can identify the positioning portion 400 through an external medical device, such as an X-ray device, to locate the position of the balloon 100 in the blood vessel, so that the multi-guidewire balloon dilatation catheter structure 10 can meet the surgical needs. Particularly, in the preferred embodiment, there are two positioning portions 400. It is known that two points determine a line. The position and direction of the axis of the balloon 100 can be accurately identified by providing the two positioning portions 400, thereby achieving precise positioning.

Particularly, referring to FIGS. 2 and 3, the multi-guidewire balloon dilatation catheter structure 10 further comprises a guidewire member 300, which is provided outside the balloon 100 and which is at least partially located at the distal end of the balloon 100, and the second guidewire channel 310 are at least partially provided inside the guidewire member 300.

In this embodiment, the multi-guidewire balloon dilatation catheter structure 10 is used by the guidewire member 300 partially located at the D end of the balloon 100. When the balloon 100 is dilated, the outer wall of the balloon 100 can drive the guidewire to come into contact with the inner wall of the blood vessel or cut the lesion on the inner wall of the blood vessel, and can anchor the guidewire by the dilatation of the balloon 100. Particularly, the guidewire member 300 can be integrated with the balloon 100, and a cavity communicating with the second guidewire channel 310 or forming the second guidewire channel 310 is provided in the guidewire member 300, which works with the guidewire through the cavity; the guidewire member 300 can also be connected to the balloon 100 by means of detachable connection such as sleeving, snap-fitting, or adhesion. When the guidewire member 300 is connected to the balloon 100 by means of detachable connection, the guidewire member 300 can be separated from the balloon 100 during manufacturing. The guidewire member 300 and the balloon 100 are connected and installed only when the second guidewire channel 310 is needed.

In another embodiment, there are at least two guidewire members 300, and two of the guidewire members 300 are respectively provided at opposite ends of the balloon 100.

Referring to FIG. 5, there are two guidewire members 300 in this embodiment, and they are respectively provided at opposite ends of the balloon 100. When the multi-guidewire balloon dilatation catheter structure 10 of this embodiment is for use, the two guidewire members 300 can be used to work with a guidewire to improve the smoothness of movement of the multi-guidewire balloon dilatation catheter structure 10, or a plurality of guidewires can also be used to work with the two guidewire members 300 respectively to meet the corresponding needs to enhance the function of the multi-guidewire balloon expansion catheter structure 10. The use effect is good.

Particularly, the second guidewire channel 310 is at least partially parallel to the first guidewire channel 210.

In this embodiment, the first guidewire channel 210 and the second guidewire channel 310 can be parallel to the central axis of the multi-guidewire balloon dilatation catheter structure 10 to ensure the smoothness of movement of the multi-guidewire balloon dilatation catheter structure 10 along the guidewire, thereby preventing the guidewire from being bent in the multi-guide wire balloon dilatation catheter structure 10 and achieving simple effect and good use effect. In some embodiments, there may also be an included angle between the second guidewire channel 310 and the extending direction of the first guidewire channel 210, so that when the guidewire is inserted into the second guidewire channel 310, the guidewire is tilted relative to the first guidewire channel 210 to meet different surgical needs, which is not defined herein.

Referring to FIGS. 2 and 3, the multi-guidewire balloon dilatation catheter structure 10 in this embodiment further comprises a tip tube 500, which is located at the front end of the balloon 100 and which can be connected to the connection portion 120 of the balloon 100.

In this embodiment, the tip tube 500 is connected to the connecting portion 120 and communicated with the first guidewire channel 210. When the guidewire is inserted into the first guidewire channel 210, the guidewire can be at least partially passed through the tip tube 500 and guided through the tip tube 500.

Referring to FIG. 9, the present invention further provides a dilatation catheter mechanism 1, comprising the multi-guidewire balloon dilatation catheter structure 10 described in any embodiments above and at least one guidewire. When there is only one guidewire, the guidewire is inserted into at least one of the first guidewire 20 channel 210, the second guidewire 30 channel 310 and the third guidewire channel 320. When there are a plurality of guidewires, the first guidewire 20 channel 210, the second guidewire 30 channel 310 and the third guidewire channel 320 are inserted into at least one guidewire respectively. In the dilatation catheter mechanism 1 of this embodiment, the multi-guidewire balloon dilatation catheter structure 10 is provided in such a way that the structure is inserted into at least one guidewire, thereby realizing the functions of guiding, cutting and anchoring of the multi-guidewire balloon dilatation catheter structure 10, and is good in use effect.

Referring to the first embodiment shown in FIG. 6, there is only one guidewire, and the guidewire is the first guidewire 20 shown in the figure. When the dilatation catheter mechanism 1 of this embodiment is used, the first guidewire 20 can be passed through at least one of the first guidewire channel 210, the second guidewire channel 310 and the third guidewire channel 320. When the first guidewire 20 is inserted into the first guidewire channel 210, it can guide the multi-guidewire balloon dilatation catheter structure 10 to advance. When the first guidewire 20 is inserted into the second guidewire channel 310, the second guidewire channel 310 can guide the multi-guidewire balloon dilatation catheter structure 10 to advance. After the balloon 100 is dilated, the first guidewire 20 can cut the diseased tissue on the inner wall of the blood vessel under the driving force of the balloon 100, and/or the first guidewire 20 is anchored by the squeezing of the outer wall of the balloon 100 on the inner wall of the vessel.

Referring to the second embodiment shown in FIG. 7, the difference from the first embodiment is that in this embodiment, there are a plurality of multi-guidewire balloon dilatation catheter structures 10. When the dilatation catheter mechanism 1 of this embodiment is used, the plurality of multi-guidewire balloon dilatation catheter structures 10 can be provided on the first guidewire 20 in sequence. During a surgical procedure, corresponding surgical operations can be performed respectively through the plurality of multi-guidewire balloon dilatation catheter structures 10, thereby improving surgical efficiency and safety.

Referring to the third embodiment shown in FIG. 8, the difference from the second embodiment is that in this embodiment, there are two guidewires, i.e., a first guidewire 20 and a second guidewire 30. When the dilatation catheter mechanism 1 of this embodiment is used, the first guidewire 20 is placed in the blood vessel, and then the first guidewire channel 210 of the first multi-guidewire balloon dilatation catheter structure 10 is inserted into the first guidewire 20, which drives the multi-guidewire balloon dilatation catheter structure 10 to move to the lesion. Then, the second guidewire 30 is inserted into the second guidewire channel 310 of the first multi-guidewire balloon dilatation catheter structure 10, and advances to the lesion together with the first multi-guidewire balloon dilatation catheter structure 10. After the balloon 100 of the first multi-guidewire balloon dilatation catheter structure 10 is dilated, the first guidewire 20 can be anchored in the position of the lesion, the second multi-guidewire balloon dilatation catheter structure 10 can move in coordination with the second guidewire 30 to meet the corresponding surgical requirements, thereby improving surgical efficiency and safety.

In other embodiments, the dilatation catheter mechanism 1 may also be provided with a third guidewire, a fourth guidewire, etc. A plurality of multi-guidewire balloon dilatation catheter structures 10 are inserted into a plurality of guidewires in such a way that the guidewires can be inserted into the first guidewire channel 210 and/or the second guidewire channel 310 of the plurality of multi-guide wire balloon dilatation catheter structures 10 to achieve the purpose of guiding, anchoring and cutting. The combination of the multi-guidewire balloon dilatation catheter structures 10 and the guidewires is not defined herein.

Referring to FIG. 9, in this embodiment, the dilatation catheter mechanism 1 further comprises a hypotube 40 and a catheter hub 50. The catheter hub 50 is used to carry the hypotube 40, and the D end of the hypotube 40 is connected to the catheter 200.

The present invention further provides a medical device, comprising the multi-guidewire balloon dilatation catheter 10 in any one of the embodiments described above, or the dilatation catheter mechanism 1 described in any one of the embodiments described above.

It can be understood that, in the medical device of this embodiment, when the multi-guidewire balloon dilatation catheter structure 10 of this embodiment is used, at least one guidewire can be connected through the multi-guidewire balloon dilatation catheter structure 10. The multi-guidewire balloon dilatation catheter structure 10 can be guided by means of the cooperation of the guidewire and the first guidewire channel 210 to achieve the corresponding surgical function. When the guidewire is inserted into the second guidewire channel 310, the guidewire is at least partially located outside the balloon 100 and can guide the multi-guidewire balloon dilatation catheter structure 10 to advance. After the balloon is dilated, the guidewire can be driven to cut the diseased tissue on the inner wall of the blood vessel, or the guidewire can be anchored by the squeezing of the outer wall of the balloon 100 on the inner wall of the vessel, so as to facilitate the fitting of the subsequent devices and the guidewire. When the multi-guidewire balloon dilatation catheter structure 10 works with two guidewires, the two guidewires can be passed through the first guidewire channel 210 and the second guidewire channel 310 respectively to meet the surgical needs. In the medical device of this embodiment, each guidewire channel can be inserted into the guidewire by providing the first guidewire channel 210 and the second guidewire channel 310, thereby realizing simultaneous execution of guiding, cutting and anchoring functions of the multi-guidewire balloon dilatation catheter structure 10. The medical device is simple in structure and good in use effect.

In the description of the embodiments of the present invention, it should be noted that the orientation or positional relationship indicated by the terms such as "center", "longitudinal", "transverse", "up", "down", "front", "rear", "left", "right", "vertical", "horizontal", "top", "bottom", "inside", and "outside" are based on the drawings. They are only for the convenience of describing the embodiments of the present invention and simplified description. They are not intended to indicate or imply that the devices or elements referred to must have a particular orientation, be constructed and operated in a particular orientation, and therefore they should not be construed as a restriction on the embodiments of the invention. Furthermore, the terms "first", "second", and "third" are merely intended for descriptive purposes only and should not be construed as an indication or implication of relative importance.

In the description of the embodiments of the present invention, it should be noted that, unless otherwise expressly specified and defined, the terms "connected" and "connection" should be understood in a broad sense, for example, it may be fixed connection, or detachable connection, or integral connection, or mechanical connection, or electrical connection; it may be directly connected or indirectly connected through an intermediate medium. For those of ordinary skill in the art, the specific meaning of the above terms in the embodiments of the present invention may be understood on a case-by-case basis.

In the embodiments of the present invention, unless otherwise expressly specified and defined, the first feature "above" or "under" the second feature may mean that the first feature is in direct contact with the second feature, or the first feature is in indirect contact with the second feature through an intermediate medium. In addition, the first feature "above", "over" and "on" the second feature may mean that the first feature is directly above or obliquely above the second feature, or simply means that the first feature has a higher level than the second feature. The first feature "below", "beneath" and "under" the second feature may mean that the first feature is directly below or obliquely below the second feature, or simply means that the first feature has a lower level than the second feature.

In the description, the descriptions with reference to the terms, such as "one embodiment," "some embodiments," "example," "specific example," or "some examples", means specific features, structures, materials, or characteristics described in conjunction with this embodiment or example are included in at least one embodiment or example of the present invention. In the description, schematic representations of the above terms are not necessarily directed to the same embodiment or example. Furthermore, the specific features, structures, materials, or characteristics described may be combined in any or more than one embodiment or example in a suitable manner. In addition, those skilled in the art may combine the different embodiments or examples described in this description as well as the features of the different embodiments or examples if they do not contradict each other.

Finally, it should be noted that the above embodiments are only used to explain the technical scheme of the present invention, but not to define it. Although the present invention has been described in detail with reference to the foregoing embodiments, those of ordinary skill in the art should know that they can still modify the technical scheme described in the foregoing embodiments, or replace some technical features thereof equivalently. These modifications or replacements do not make the essence of the corresponding technical scheme deviate from the spirit and scope of the technical scheme of the embodiments of the present invention.

What is claimed is:

1. A multi-guidewire balloon dilatation catheter structure, comprising:
   a balloon;
   a first guidewire channel, which is used for accommodating a guidewire and which is at least partially passed through the balloon;
   a second guidewire channel, which is used for accommodating a guidewire and which is at least partially located at a distal end of the balloon; and
   a third guidewire channel, which is used for accommodating a guidewire and which is at least partially located at a proximal end of the balloon;
   a catheter, the catheter being passed through the balloon, and a guidewire exchange port being formed in an outer wall of the catheter and provided at a proximal end of multi-guidewire balloon dilatation catheter structure, wherein . . .
   the multi-guidewire balloon dilatation catheter structure is capable of receding from a distal end of the guidewire and is separated from the guidewire, and
   a plurality of multi-guidewire balloon dilatation catheter structures are simultaneously used on one guidewire.

2. The multi-guidewire balloon dilatation catheter structure according to claim 1, wherein the distance between the guidewire exchange port and the balloon along a central axis of the multi-guidewire balloon dilatation catheter structure is less than 30 mm.

3. The multi-guidewire balloon dilatation catheter structure according to claim 2, wherein the distance between the guidewire exchange port and the balloon along the central axis of the multi-guidewire balloon dilatation catheter structure is 10-20 mm.

4. The multi-guidewire balloon dilatation catheter structure according to claim 1, wherein an accommodating cavity communicated with an external air source is provided inside the balloon, and the multi-guidewire balloon dilatation catheter structure further comprises at least one positioning portion which is connected to the catheter and which is at least partially located in the accommodating cavity.

5. The multi-guidewire balloon dilatation catheter structure according to claim 1, wherein the multi-guidewire balloon dilatation catheter structure further comprises a guidewire member which is provided outside the balloon and which is at least partially located at the distal end and the proximal end of the balloon, and the second guidewire channel and the third guidewire channel are at least partially provided inside the guidewire member.

6. The multi-guidewire balloon dilatation catheter structure according to claim 5, wherein there are at least two guidewire members, and two of the guidewire members are respectively provided at opposite ends of the balloon.

7. The multi-guidewire balloon dilatation catheter structure according to claim 5, wherein the second guidewire channel or the third guidewire channel is at least partially parallel to the first guidewire channel.

8. A dilatation catheter mechanism, comprising:
at least one guidewire; and
a multi-guidewire balloon dilatation catheter structure according to claim 1; when there is only one guidewire for the multi-guidewire balloon dilatation catheter structure, the guidewire is inserted into at least one of the first guidewire channel, the second guidewire channel and the third guidewire channel, and when there are a plurality of guidewires, each guidewire of the plurality of guidewires can be inserted into the first guidewire channel, the second guidewire channel and the third guidewire channel, respectively.

9. A medical device, comprising a multi-guidewire balloon dilatation catheter structure according to claim 1, or the dilatation catheter mechanism according to claim 8.

* * * * *